United States Patent [19]

Katopodis

[11] Patent Number: 5,462,877
[45] Date of Patent: Oct. 31, 1995

[54] METHOD FOR DETERMINING LIPID BOUND SIALIC ACID IN PLASMA OR SERUM

[76] Inventor: Nonda Katopodis, 10 Greens Cir., Stamford, Conn. 06903

[21] Appl. No.: 147,881

[22] Filed: Nov. 5, 1993

[51] Int. Cl.$^6$ .......................... G01N 33/48; G01N 31/22
[52] U.S. Cl. .................. 436/93; 436/64; 436/71; 436/129; 436/178; 436/813; 435/810; 422/61
[58] Field of Search .................. 436/63, 64, 71, 436/87, 94, 93, 129, 177, 178, 813, 164; 530/420; 435/4, 18, 810; 422/61

[56] References Cited

U.S. PATENT DOCUMENTS

| | | | |
|---|---|---|---|
| 4,342,567 | 8/1982 | Katopodis et al. | 23/230 B |
| 4,748,128 | 5/1988 | Katopodis | 436/93 |
| 5,045,453 | 9/1991 | Katopodis | 435/18 |
| 5,296,346 | 3/1994 | Katopodis | 435/4 |

*Primary Examiner*—David A. Redding
*Attorney, Agent, or Firm*—Paul L. Bollo

[57] ABSTRACT

The amount of lipid bound sialic acid in a blood plasma or serum sample may be determined by an improved method, which may be automated, involving the following steps to be performed simultaneously on the sample and a standard consisting of commercially available n-acetyl nueraminic acid (NANA); diluting with a buffer; mixing the diluted sample; adding a mixture of a chlorinated lower aklyl hydrocarbon and a lower alkyl alcohol; treating by mixing and centrifuging to yield a substantially clear upper phase; treating the upper phase with a color development reagent; mixing; boiling the admixture; cooling the admixture; and determining the amount of lipid bound sialic acid present in the sample by comparing the optical density of the sample to the optical density of the NANA.

23 Claims, No Drawings

METHOD FOR DETERMINING LIPID BOUND SIALIC ACID IN PLASMA OR SERUM

BACKGROUND OF THE INVENTION

This invention concerns an improved method for the determination of lipid bound sialic acid in plasma or serum which is less expensive, less time consuming, less variable from sample to sample, and less dependent upon the skill and experience of the person performing the test. Additionally this invention concerns an improved test kit which contains a unique standard which will allow greater reproducibility of test results and more consistency throughout the world.

Much work has been done which indicates that elevated sialic acid content in blood sera of a patient is an indication of the presence of cancer. For example, U.S. Pat. No. 4,146,603 to Davidson, et al. discloses and claims a fairly complex series of procedures whereby elevated sialic acid content is a determinant with respect to cancer specific determinations.

MacBeth and Bekesi, Cancer Res. 22:1170–1176 (1962) measured plasma glycoproteins and found galactose and mannose values were seen in breast cases without metastases. Kloppel, et al., Proc. Natl. Acad. Sc. 74:3011–3013 (1977) reported 2.5-fold increases of serum sialic acid glycolipids in mice bearing transplantable mammory carcinomas and 2-fold increases in human carcinoma patients. Kloppel, et al., Am. J. Vet. Res. 39:1377–1380 (1978) also reported increases of sialic acid in 93% of 24 dogs. In leukemia AKR/J mice, Lengle, J. Natl. Cancer Inst. 62:1565–1567 (1979) found increased lipid bound sialic acid in their plasma and thymic lymphocytes. Lipid bound sialic acid levels were found increased in plasma and erythrocytes of humans bearing melanomas. Portouklian, et al., Biochem. Biophys. Res. Commun. 85:916–920 (1978). Chromatographic separation and purification on columns was followed by evaluation on chromatoplates. Silver, et al., Cancer 41:1497–1499 (1978); Cancer Res. 39:5036–5042 (1979) have reported elevated serum sialic acid values in melanoma patients that were significantly related to the tumor burden. However, 36% of patients with observable tumors showed no elevated serum sialic acid. Hogan-Ryan, et al., Br. J. Cancer 41:587–592 (1980) reporting on total bound serum sialic acid in patients with breast cancer found elevations that corresponded with tumor stage.

One specific method over which the present invention is an improvement is disclosed in the American Association for Cancer Research Annual Meeting PROCEEDINGS Vol 21, March 1980 as Abstract No. 728 by Katopodis, et al. This method requires that a 100 ul plasma sample (reduced to 50 ul) be extracted with 6 ml of a chloroform/methanol mixture, (2 to 1, volume to volume ratio). The lipid extract is then partitioned with 0.2 of its volume of water. The aqueous phase is evaporated to dryness and the residue redissolved in water. The lipid bound sialic acid is then purified by trichloroacetic acid-phosphotungstic acid precipitation and, after the removal of the supernatant from the resultant precipitate, the precipitate is determined by the Svennerholm and Miettien method (Svennerholm, Quantitative Estimation of Sialic Acid..., Biochem. Biophys, Acta. 24, pp. 604–611 (1957)).

Another specific method over which the present invention is an improvement is disclosed in Katopodis and Stock, U.S. Pat. No. 4,342,567, issued Aug. 3, 1982. This method is similar to the foregoing but requires only about 50 ul of sample rather than the 100 ml required by the prior art method. The drying step is eliminated and there is no use of trichloracetic acid. Phosphotungstic acid is used alone.

This method suffers from a number of disadvantages including the following: the need for a precisely defined 44.7 ul starting sample; lipid bound sialic acid is lost during the tube inversion step creating reduced final values; precipitation of the lipid bound sialic acid with phosphotungstic acid is not complete, which is a particular problem when working with samples in which the amount exceeds normal values by only small amounts (e.g. early in cancer development); the rapidity of the test is limited by the 5 minutes waiting time after phosphotungstic acid addition and the cost of the test is not as low as is desirable. Another method over which the present invention is an improvement is disclosed in Katopodis, U.S. Pat. No. 4,748,128, issued May 31, 1988. This prior method consists of the following steps:

(a) diluting a predetermined volume of a blood plasma or serum with distilled water to a volume about four times that of the predetermined volume;

(b) mixing the diluted sample for a suitable period of time to obtain a substantially homogeneous sample;

(c) cooling the mixed, diluted sample to about 0 degrees to 5 degrees C.;

(d) adding to the cooled sample a mixture of a chlorinated lower alkyl hydrocarbon and a lower alkyl alcohol, the volume of the mixture added being about sixty times the predetermined volume of the blood plasma or serum sample, and the volume ratio of chlorinated hydrocarbon to alcohol in the mixture being about 2:1 and its temperature about 0 degrees to 5 degrees C.;

(e) mixing the resulting admixture for a suitable period of time to dissolve matter present in the sample in the chlorinated hydrocarbon/alcohol mixture;

(f) diluting the admixture with deionized distilled water at a temperature from about 0 degrees to 5 degrees C., the volume added being about ten times the predetermined volume of the blood plasma or serum sample;

(g) treating the diluted admixture for a suitable period of time to permit formation of a substantially clear upper phase;

(h) separately recovering from the clear upper phase so formed a predetermined volume of the upper phase;

(i) adding to the predetermined volume of the upper phase an amount of a mixture of a protein-precipitating agent and an adsorbing material, the amount of mixture being effective to cause precipitation of the lipid bound sialic acid and to adsorb the precipitated lipid bound sialic acid;

(j) mixing the resulting admixture;

(k) separately recovering the resulting adsorbed precipitate;

(l) suspending the precipitate in a suitable volume distilled water; and (m) adding to the suspended precipitate a volume of resorcinol reagent, mixing, boiling for 15 minutes, cooling for 10 minutes in an ice bath, centrifuging, adding a mixture of butylacetate and n-butanol (85:15 v/v) in a volume about twice the volume of the resorcinol reagent, mixing, centrifuging, separating the organic layer, reading at 580 nm the extracted blue color present in the organic layer, and determining the amount of lipid bound sialic acid by comparing the optical density reading obtained at 580 nm to a standard curve developed from a known sample of n-acetyl neuraminic acid (NANA) under the same conditions and applying the formula:

$$LSA\ (mg/100\ ml\ plasma) = (x \cdot 10^5 ul)/y \cdot z\ ul \cdot 1000$$

where x=NANA read from the standard curve, y=the volume of the upper phase recovered divided by the total volume of the entire upper phase and z=the predetermined volume of the blood plasma or serum sample.

The present invention provides an improved method for determining the amount of lipid bound sialic acid present in a sample of plasma or serum. The present invention is simpler, more economical, faster, more easily automated, and is suitable for the preparation of monoclonal antibodies due to its purity. It requires less chemical reagents and is superior in terms of specificity and sensitivity than the methods of the prior art. The procedure of the present invention differs significantly from known methods in that the present invention eliminates the need to use a protein precipitating agent and eliminates the need to use a special standard. The present invention reads the optical density of standard commercially available n-acetyl neuraminic acid (NANA) and thus eliminates the need to construct a standard curve. This enhances reproducibility from laboratory to laboratory and enables the user to more quickly and more accurately determine the level of sialic acid in the sample.

The prior art requires the use of a protein precipitating agent such as phosphotungstic acid and an adsorbing material to cause the precipitation of the lipid bound sialic acid. The present invention does not require this step as it has been found that it is unnecessary where the ratio of the chlorinated hydrocarbon to alcohol is approximately 1:1 in the buffered solution.

Significantly the present invention provides an improved procedure for determining the concentration of lipid bound sialic acid in a sample of human blood plasma or serum by comparing the sample with a standard consisting of n-acetyl neuraminic acid (NANA) in commercially available form rather than human or animal blood plasma. Commercially available NANA has the advantage of being readily available, is extremely stable and has a long shelf life. It also eliminates the need to construct a standard curve for the standard as in the prior art. It is also superior to the methods of the prior art since the elimination of the protein precipitating reagent enables the LSA fraction to be used easily for the preparation of specific monoclonal antibodies.

Finally, the chemistry of the present invention eliminates the need to use a mixture of butylacetate and n-butanol as in the prior art. In addition to the making the test less expensive, it avoids the need to work with this mixture which has a foul smell, causes a burning sensation in the nasal membrane of the technician and is generally difficult to work with.

SUMMARY OF THE INVENTION

The present invention provides a method for extracting lipid bound sialic acid from a sample of human blood plasma or serum and determining the amount of lipid bound sialic acid present in the sample which includes the following steps:

(a) diluting a predetermined volume of a blood plasma or serum sample with buffer solution to a volume about five (5) times that of the predetermined volume;

(b) mixing the diluted sample for a suitable period of time to obtain a substantially homogeneous sample;

(c) adding to the sample a mixture of a chlorinated lower alkyl hydrocarbon and a lower alkyl alcohol, the volume of the mixture added being about twenty (20) times the predetermined volume of the blood plasma or serum sample, and the volume ratio of chlorinated hydrocarbon to alcohol in the mixture being about 1:1;

(d) mixing the resulting admixture for a suitable period of time to dissolve matter present in the sample in the chlorinated hydrocarbon/alcohol/buffer mixture;

(e) centrifuging the admixture for a suitable period of time at a suitable speed to permit formation of a substantially clear upper phase;

(f) separately recovering from the clear upper phase so formed a predetermined volume of the upper phase;

(g) adding to the predetermined volume of the clear upper phase a color development reagent;

(h) mixing the resulting admixture;

(i) boiling the admixture;

(j) cooling the admixture;

(k) mixing, then centrifuging said admixture, separating the clear supernatant from the precipitated material; and (l) determining the amount of lipid bound sialic acid present in the supernatant and thereby the amount present in the blood plasma or serum sample.

The determination of the amount of lipid bound sialic acid in the sample is made by comparing the optical density of the sample to that of a standard consisting of commercially available NANA which has been processed by the identical procedure and at the same time as the sample.

The concentration of lipid bound sialic acid in the sample is found by multiplying the optical density of the sample times the known concentration of the standard (in mg/100 ml) and dividing the product by the optical density of the standard.

The improved procedure of the invention provides improved reproducibility of the test and improved accuracy of the test results in any laboratory because the test sample and the known standard are treated with exactly the same techniques. Thus variations between the test results for the sample and the standard which are due to variations in the procedures or techniques used in testing the sample are eliminated.

This invention also provides a method and kit for diagnosing cancer in a human subject which comprises determining the amount of lipid bound sialic acid in a sample of a subject's blood plasma or serum and comparing the amount obtained with values obtained for subjects known to have cancer.

Alternatively the method and kit of this invention may be used to regularly determine the amount of lipid bound sialic acid present in a subject's blood plasma or serum and thus to monitor the progress of therapy of a subject by comparing each amount so determined with amounts previously determined for the subject.

Another aspect of the invention concerns a method of diagnosing cancer in a human subject which comprises determining the amount of lipid bound sialic acid in a sample of the subject's plasma or serum according to the method of the present invention and comparing the amounts so determined with values obtained for subjects known to have cancer, or alternatively, comparing the amount so determined with values obtained over a period of time for the same subject.

The invention also provides a method for monitoring the progression of cancer in a subject which comprises determining at regular time intervals the amount of lipid bound sialic acid in a sample of the subject's blood plasma or serum according to the method of the present invention and comparing the amount so determined with amounts previously obtained for the subject.

Furthermore, this invention provides an improved cancer diagnostic kit comprising a container containing a mixture of a lower alkyl alcohol and chlorinated lower alkyl hydrocarbon; a container of prediluted resorcinol reagent; a container of NANA in commercially available form and having a known concentration of lipid bound sialic acid; and instructions enabling the user of the kit to conduct the test and compare it to the standard provided to determine the amount of lipid bound sialic acid in the sample without variations between the sample and the standard resulting from the techniques or procedures used by the person conducting the test.

The invention also provides a method for preparation of a pure fraction (upper phase) which after lyophilyzation will provide the basic material for the preparation of the monoclonal antibodies, since the natural proteins of the plasma or serum are not destroyed by the extraction and precipitation with phosphotungstic acid as in the prior art methods.

DETAILED DESCRIPTION OF THE INVENTION

The amount of lipid bound sialic acid in a sample of human blood plasma or serum may be determined and the amount so determined used as a diagnostic indicator of cancer. A preliminary step to the method is to obtain a sample to be tested. The sample will typically be recovered from whole blood drawn from a subject and treated using methods which are well known and described in the prior art. See, for example, Katopodis, U.S. Pat. No. 4,748,128.

The initial step of the method of the present invention is to dilute a predetermined volume of a blood plasma or serum sample with buffer solution. The volume dilution is about five times the volume of initial plasma sample. Thus, if the initial plasma or serum sample is 50 ul in a small tube or container, the amount of distilled water added is about 250 ul to produce about 300 ul of diluted sample, i.e., about six times the volume of the initial sample.

The diluted sample is mixed, e.g., by vortexing, for a suitable time to obtain a substantially homogeneous sample, e.g., at least 5 seconds.

A mixture of a chlorinated lower alkyl hydrocarbon and a lower alkyl alcohol in which the volume ratio of chlorinated hydrocarbon to alcohol is about 1 to 1 is then added to the sample. The volume of the chlorinated hydrocarbon and alcohol mixture added is about twenty times the original, i.e., predetermined, volume of the plasma sample and its temperature is room temperature. Thus, if the original sample volume is 50 ul, then the volume of mixture added is about 1.0 ml. Suitable chlorinated hydrocarbons include chloroform, methylene chloride and ethylene chloride, chloroform being presently preferred. The lower alkyl alcohol may be methanol, ethanol, propanol, n-butanol, isopropanol, isobutanol or isoamyl alcohol. The greater the number of carbon atoms in the alcohol, the less effective the mixture is in terms of lipid bound sialic acid extraction as opposed to total sialic acid extraction. Therefore, the preferred alcohol is methanol since the other alcohols extract higher amounts of total sialic acid and other contaminants, and therefore reduce the diagnostic value of the test.

The resulting admixture is then mixed for a suitable period of time by vortexing for approximately 10 seconds to dissolve matter present in the sample in the chlorinated hydrocarbon/alcohol mixture. The mixture is then centrifuged for about five minutes at about 3500 rpm to yield a substantially clear upper phase.

A predetermined volume of the upper phase is then separately recovered from the substantially-clear upper phase so formed, preferably by removing the upper phase from the lower phase and discarding the latter. The predetermined volume so recovered will depend upon the volume of the original plasma sample. Thus, if the original, i.e. predetermined, plasma volume is about 50 ul, the volume of upper phase separately recovered will be about 200 ul.

A suitable volume of a color development agent, preferably resorcinol, e.g., 1.0 ml, is added to the mixture which is then treated by vortexing for about 5 seconds. The mixture is then boiled by placing the tube in which is contained in a vigorously boiling waterbath for a period of about 15 minutes after the water has reached 100 degrees C. and then cooled by placing the tube in cold water for about 5 minutes. Thereafter, the mixture is centrifuged for at least 5 minutes at about 3500 rpm. The concentration of the liquid bound sialic acid is then determined by separating the clear supernatant, reading at 580 nm the extracted blue color present therein, reading the optical density of the known standard i.e. commercially available NANA, which has been treated in exactly the same manner as the sample and simultaneously therewith, and applying the formula:

$$LSA \text{ (mg/100 ml plasma)} = \frac{A \times B}{C}$$

Where A=the known value of the standard in mg/100 ml; B= the optical density of the unknown sample; and C=the optical density of the standard.

Of crucial importance to the present invention is the discovery that the buffered solution of methanol and chloroform in a 1 to 1 ratio provides a test having greater sensitivity and eliminates the need for a protein precipitating reagent. This is due to the fact that it has been found that this ratio produces an upper phase which is much larger in volume and virtually clear of contaminants. The importance of a greater volume of the clear upper phase is that the greater volume is much easier for the technician to work with and allows several tests to be made from the same upper phase. Table I demonstrates the greater sensitivity of the test of the present invention where the methanol and chloroform are in a 1:1 ratio and a decreased sensitivity as the ratio moves towards a 45:55 relationship of either methanol to chloroform or of chloroform to methanol. When the ratio of methanol to chloroform is increased to 60:40 there is a very poor separation with an extremely contaminated upper phase which cannot be used to carry out the test of the invention. As seen from Table I, when the ratio of methanol to chloroform is increased to 70:30 there is no separation at all.

Table II demonstrates the effect of the ratio of methanol to chloroform on the volume of the upper phase. Table II assumes a specimen size of 1300 microliters. It can be seen from Table II that at a ratio of 50:50, the clear upper phase of the mixture is 700 microliters and the lower phase is 600 microliters. When the ratio of methanol to chloroform is increased to 52.5:47.5 the respective volumes of the two phases remain approximately the same. When the ratio of methanol to chloroform is increased to 55:45 the volume of the upper phase increases to 760 and when the ratio is increased to 60:40 the volume increases to 840 microliters although separation is extremely poor and the upper phase is not clear. At a ratio of 70:30 there is no separation at all. Conversely, when the ratio of methanol to chloroform is decreased to 48:52; the volume of the upper phase is reduced to 600 microliters while the lower phase is increased to 700 microliters. When the ratio of methanol to chloroform is reduced to 45:55 the volume of the upper phase is further reduced to 500 microliters while the volume of the lower phase is increased to 800 microliters. Thus it can be seen from Table I and Table II that the optimum combination of the increased sensitivity to the existence of lipid bound sialic acid and the largest volume of the clear upper phase occurs when the ratio of methanol to chloroform is 50:50 or 1:1.

Table III also demonstrates the increased sensitivity of the test of the present invention by means of the higher positive identification rate of the present invention over that of the test contained in the prior art such as U.S. Pat. No. 4,748,128 to Katopodis. Table III shows tests of 532 patients being tested for various types of tumors of which 343 are known to have positive markers for the presence of those tumors from other tests. The test of the present invention identified on average 79% of those known to have positive markers for the presence of tumors while the test of the prior art such as U.S. Pat. No. 4,748,128 Katopodis, identified only 52%. Thus the test of the present invention shows an increased sensitivity of 27% over those of the prior art in detecting the presence of cancerous tumors. (See Tables I, II and III)

TABLE I

EFFECT OF RATIO OF METHANOL/CHLOROFORM ON LSA VALUES

| | Ratio of Methanol to Chloroform (Methanol/Chloroform) | | | | | | |
|---|---|---|---|---|---|---|---|
| Sample | 45/55 | 48/52 | 50/50 | 52.5/47.5 | 55/45 | 60/40 | 70/30 |
| #1 | 8.0* | 8.3 | 8.9 | 7.2 | 5.1 | phase separation too poor for test | no separation |
| #2 | 10.3 | 12.2 | 13.4 | 12.0 | 10.4 | | |
| #3 | 20.7 | 23.9 | 24.3 | 21.2 | 17.6 | | |
| #4 | 22.0 | 25.5 | 26.9 | 20.3 | 18.5 | | |
| #5 | 43.1 | 46.5 | 48.3 | 39.7 | 27.9 | | |

*Concentrations of lipid bound sialic acid in samples (mg/100 ml)

TABLE II

EFFECT OF RATIO OF METHANOL TO CHLOROFORM ON VOLUME OF UPPER PHASE OF A 1300 MICROLITER SAMPLE

| | Ratio of Methanol to Chloroform | | | | | | |
|---|---|---|---|---|---|---|---|
| | 45:55 | 48:52 | 50:50 | 52.5:47.5 | 55:45 | 60:40 | 70:30 |
| Volume of Upper Phase | 500 | 600 | 700 | 700 | 760 | poor separation 460 | no separation 1300 |
| Volume of Lower Phase (in microliters) | 800 | 700 | 600 | 600 | 540 | 840 | no separation 1300 |

TABLE III

INCREASED SENSITIVITY OF INVENTION IN IDENTIFYING PATIENTS KNOWN TO HAVE CANCER FROM OTHER TEST MARKERS

| Type of Tumor | Number of Patients Tested | Number of Patients with Positive Disease | Percent Positive Disease Identified | |
|---|---|---|---|---|
| | | | Prior Art Test | Test of Present Invention |
| Breast | 168 | 62 | 37% | 66% |
| Colon | 92 | 71 | 38 | 56 |
| Ovary | 70 | 53 | 66 | 91 |
| Lung | 53 | 40 | 75 | 87 |
| Prostate | 45 | 39 | 59 | 79 |
| Melonoma | 24 | 5 | 20 | 80 |
| Misc. | 78 | 73 | 68 | 95 |
| Total | 532 | 343 | 52% (average) | 79% (average) |

What is claimed is:

1. A method of extracting lipid bound sialic acid from human blood plasma or serum and determining the amount of lipid bound sialic acid in a sample of human blood plasma or serum which comprises the following steps:

(a) diluting a predetermined volume of a blood plasma or serum sample with buffer solution to a volume about six (6) times that of the predetermined volume of the sample;

(b) mixing the diluted sample for a suitable period of time to obtain a substantially homogeneous sample;

(c) adding to the sample a mixture of a chlorinated lower alkyl hydrocarbon and a lower alkyl alcohol, the volume of the mixture added being about twenty (20) times the predetermined volume of the blood plasma or serum sample, and the volume ratio of chlorinated hydrocarbon to alcohol in the mixture being about 1:1;

(d) mixing the resulting admixture for a suitable period of time to dissolve matter present in the sample in the chlorinated hydrocarbon/alcohol/buffer mixture;

(e) centrifuging the admixture for a suitable period of time at a suitable speed to permit formation of a substantially clear upper phase;

(f) separately recovering from the clear upper phase so formed a predetermined volume of the upper phase;

(g) adding to the predetermined volume of the clear upper phase a color development reagent;

(h) mixing the resulting admixture;

(i) boiling the admixture;

(j) cooling the admixture;

(k) mixing, then centrifuging said admixture, separating the clear supernatant from the precipitated material; and (l) determining the amount of lipid bound sialic acid present in the supernatant and thereby the amount present in the blood plasma or serum sample.

2. A method according to claim 1, wherein in step (a) the predetermined volume is about 50 ul and is diluted with about 250 ul of buffer solution.

3. A method according to claim 1, wherein in step (b) the mixing comprises vortexing for at least 5 seconds.

4. A method according to claim 2, wherein in step (c) the volume of the added mixture is about 1 ml.

5. A method according to claim 1, wherein in step (c) the lower alkyl alcohol is methanol, ethanol, propanol, n-butanol, isopropanol, isobutanol or isoamyl alcohol.

6. A method according to claim 5, wherein in step (c) the lower alkyl alcohol is methanol.

7. A method according to claim 1, wherein in step (c) the chlorinated lower alkyl hydrocarbon is chloroform.

8. A method according to claim 1, wherein in step (d) the mixing comprises vortexing for at least 10 seconds.

9. A method according to claim 1, wherein in step (e) the centrifuging is carried out at about 3500 rpm for at least 5 minutes.

10. A method according to claim 1, wherein in step (f) the separately recovering comprises removing the upper phase from the lower phase.

11. A method according to claim 2, wherein in step (f) the predetermined amount of the upper phase is about 200 microliters.

12. A method according to claim 2, wherein in step (g) the predetermined volume of the color development reagent is about 1 ml.

13. A method according to claim 1, wherein in step (g) the color development reagent is resorcinol.

14. A method according to claim 1, wherein in step (h) the mixing comprises vortexing for about 5 seconds.

15. A method according to claim 1, wherein in step (i) the boiling of the mixture is carried out for about 15 minutes.

16. A method according to claim 1, wherein in step (j) the mixture is cooled for about 5 minutes.

17. A method according to claim 1, wherein in step (k) the mixing is carried out by vortexing for 5 seconds and the centrifuging is carried out for 5 minutes at 3500 rpm.

18. A method according to claim 1, wherein in step (l) the amount of lipid bound sialic acid is determined by reading at 580 nm the extracted blue color present in the supernatant, determining the amount of lipid bound sialic acid by comparing the reading obtained at 580 nm to that obtained for a standard having a known concentration of lipid bound sialic acid and applying the formula LSA=A×B/C where A=the known concentration of the standard, B=the optical density of the sample and C=the optical density of the standard.

19. A method according to claim 18, wherein the known standard is tested exactly the same as, and simultaneously with, the sample in accord with the method of claim 1.

20. A method according to claim 18, wherein the standard is commercially available n-acetyl neuraminic acid (NANA).

21. A cancer diagnostic kit comprising a container of a mixture of chlorinated lower alkyl hydrocarbon and lower alkyl alcohol (1:1 v/v); a container of resorcinol reagent; a container of buffer solution; a container of commercially available n-acetyl neuraminic acid solution having a known concentration of lipid bound sialic acid; and written instructions for treating the sample and the standard according to the method of claim 1.

22. A cancer diagnostic kit according to claim 21, wherein the lower alkyl alcohol is methanol and the lower alkyl hydrocarbon in chloroform.

23. In a method for determining the amount of lipid bound sialic acid in a sample of human blood plasma or serum according to the method of claim 1 the treatment of the known standard at the same time and in the same manner as the sample with the effect that discrepancies in the test results attributable to variations in the techniques used in the test of the sample and the standard are eliminated.

* * * * *